United States Patent [19]

Baldwin et al.

[11] Patent Number: 5,112,824
[45] Date of Patent: May 12, 1992

[54] BENZOFURAN COMPOUNDS AS CLASS III ANTIARRHYTHMIC AGENTS

[75] Inventors: John J. Baldwin, Gwynedd Valley; Harold G. Selnick, Ambler; Gerald S. Ponticello, Lansdale; David C. Remy; David A. Claremon, both of North Wales; Jason M. Elliott, Blue Bell, all of Pa.

[73] Assignee: Merck & Co., Inc., Rahway, N.J.

[21] Appl. No.: 730,332

[22] Filed: Jul. 15, 1991

Related U.S. Application Data

[63] Continuation-in-part of Ser. No. 447,941, Dec. 8, 1989, Pat. No. 5,032,604.

[51] Int. Cl.⁵ .................. A61K 31/495; A61K 31/445; C07D 403/00; C07D 211/68
[52] U.S. Cl. ..................... 514/253; 514/252; 514/254; 514/318; 514/322; 544/295; 544/364; 544/368; 546/159; 546/193; 546/194; 546/199
[58] Field of Search ............. 544/295, 364, 368; 546/193, 159, 194, 199; 514/252, 253, 318, 322

[56] References Cited

U.S. PATENT DOCUMENTS

| | | | |
|---|---|---|---|
| 4,544,654 | 10/1965 | Davey et al. | 514/210 |
| 4,629,739 | 12/1966 | Davey et al. | 514/605 |
| 4,721,809 | 1/1988 | Buzby et al. | 564/82 |
| 4,783,471 | 11/1988 | Carr et al. | 514/317 |
| 4,788,196 | 11/1988 | Cross et al. | 514/252 |
| 4,797,401 | 1/1989 | Kemp et al. | 514/255 |
| 4,804,662 | 2/1989 | Nickisch et al. | 514/252 |
| 4,806,536 | 2/1989 | Cross et al. | 514/252 |
| 4,806,555 | 2/1989 | Lamsford et al. | 514/652 |

FOREIGN PATENT DOCUMENTS

| | | |
|---|---|---|
| 235752 | 9/1987 | European Pat. Off. . |
| 242173 | 10/1987 | European Pat. Off. . |
| 281254 | 9/1988 | European Pat. Off. . |
| 284384 | 9/1988 | European Pat. Off. . |
| 285284 | 10/1988 | European Pat. Off. . |
| 288277 | 10/1988 | European Pat. Off. . |
| 296560 | 12/1988 | European Pat. Off. . |
| 300908 | 1/1989 | European Pat. Off. . |
| 307121 | 3/1989 | European Pat. Off. . |
| 3633977 | 4/1988 | Fed. Rep. of Germany . |

*Primary Examiner*—Cecilia Shen
*Attorney, Agent, or Firm*—Donald J. Perrella; William H. Nicholson

[57] ABSTRACT

Compounds of structural formula:

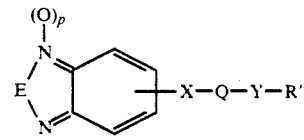

wherein R' is hydrogen or an aromatic ring system, and Q is a substituted nitrogen or a nitrogen containing heterocycle, X and Y are bridging groups and p is 0 or 1, and E is —S— or —O—, are Class III antiarrhythmic agents.

6 Claims, No Drawings

BENZOFURAN COMPOUNDS AS CLASS III ANTIARRHYTHMIC AGENTS

RELATED APPLICATION

The present patent application is a continuation-in-part of our copending patent application Ser. No. 447,941 filed Dec. 8, 1989, now U.S. Pat. No. 5,032,604.

SUMMARY OF THE INVENTION

This invention is concerned with novel compounds of the class with structural formula:

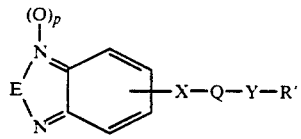

or a pharmaceutically acceptable salt thereof, wherein $R^1$ is hydrogen or an aromatic ring system, E is —S— or —O—, and X and Y are bridging groups such as alkylene or a bond, and Q is a substituted nitrogen atom or a 5–7 membered nitrogen heterocycle such as piperidine or piperazine, and p is 0 or 1.

These compounds are useful in the treatment of arrhythmia.

The invention is also concerned with novel processes for preparing the novel compounds; pharmaceutical formulations comprising one or more of the novel compounds as an active antiarrhythmic agent either as the sole active ingredient or in combination with one or more other cardiovascular agents such as a β-blocker or other antiarrhythmic agent; and a method of treating arrhythmia by administration of one of the novel compounds to a patient in need of such treatment.

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, those having both satisfactory effects and high safety have not been obtained. For example, antiarrythmic agents of Class I according to the classification of Vaughan-Williams which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrhythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain patients. Also, amiodarone is severly limited by side effects. Drugs of this class are expected to be effective in preventing ventricular fibrillations. Pure class III agents, by definition, are not considered to cause myocardial depression or an induction of arrhythmias due to the inhibition of the action potential conduction as seen with Class I antiarrhythmic agents.

A number of antiarrhythmic agents have been reported in the literature, such as those disclosed in:

(1) EP 397,121-A,
(2) EP 300,908-A,
(3) EP 307,121,
(4) U.S. Pat. No. 4,629,739,
(5) U.S. Pat. No. 4,544,654,
(6) U.S. Pat. No. 4,788,196,
(7) EP application 88302597.5,
(8) EP application 87306922.3,
(9) EP application 88302598.3,
(10) EP application 88302270.9,
(11) EP application 88302600.7,
(12) EP application 88302599.1,
(13) EP application 88300962.3,
(14) EP application 235,752,
(15) DE 3633977-A1,
(16) U.S. Pat. No. 4,804,662,
(17) U.S. Pat. No. 4,806,555,
(18) U.S. Pat. No. 4,806,536.

DETAILED DESCRIPTION OF THE INVENTION

The novel compounds of this invention have structural formula:

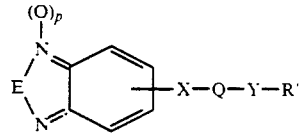

or a pharmaceutically acceptable salt thereof, wherein:

Q is a 5-7 membered heterocycle with one or two nitrogen atoms such as piperidine, piperazine, pyrrolidine, imidazolidine, hexahydroazepine, hexahydrodiazepine, 2,5-diazabicyclo[2.2.2]octane, or morpholine or substituted nitrogen

wherein R is H or $C_{1-6}$alkyl;

X and Y are independently:

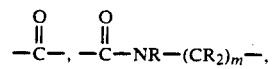

—(CR$_2$)—$_m$, —O(CR$_2$)$_m$—, —(CR$_2$)$_m$O—, —SO$_2$—, —CH$_2$NR(CR$_2$)$_m$ or, when p is 0, a bond, and R is H or $C_{1-6}$ alkyl;

m is 1, 2 or 3;

E is —O— or —S—;

p is 0, or 1;

$R^1$ is hydrogen or a mono- or bicyclic structure selected from:

1) 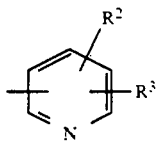
2) 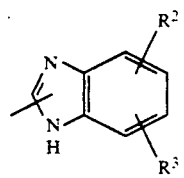
3) 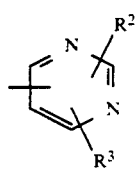
4) 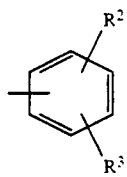
5) 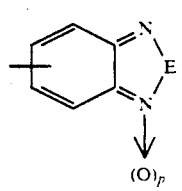
wherein E is O or S
6) 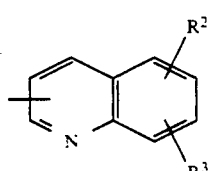
7) 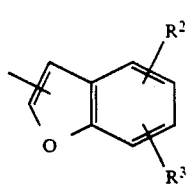
8) 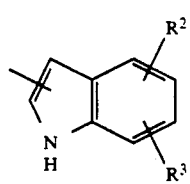
9) 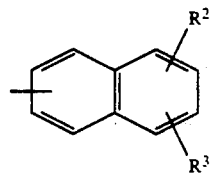
10) 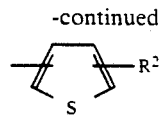
11) 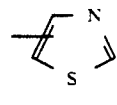
12) 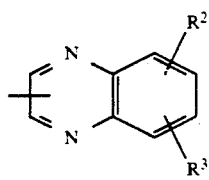
13) 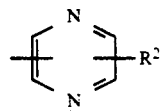
14) 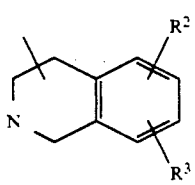
15) 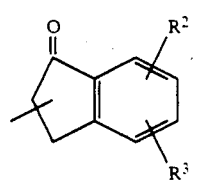
16) 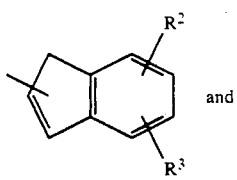 and
17) 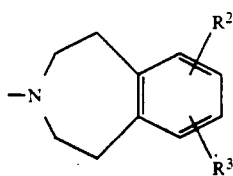
$R^2$ and $R^3$ are independently selected from:
1) hydrogen,
2) $C_{1-3}$ alkyl, either unsubstituted or substituted with
  a) —$N(R)_2$,
  b) —$CON(R)_2$,
  c) —$CO(C_{1-6}alkyl)$,
  d) —$O(C_{1-6}alkyl)$,
  e) —OH, or
  f) —$S(O)_n(C_{1-6}alkyl)$, wherein n is 0, 1 or 2;
3) $C_{1-3}$ alkoxy,
4) —$N(R)SO_2C_{1-6}alkyl$,
5) —$N(R)SO_2(CH_2)_nCO_2 C_{1-6}alkyl$,
6) —$NO_2$,
7) —$N(R)COC_{1-3}alkyl$,
8) —$N(R)SO_2$—$C_6H_4$—R
9) —NHCO—$C_6H_4$—R, 10) —N(R)$_2$.
11) halo such as Cl, Br, F, or I,
12) —C$_{2-6}$alkanoyl,
13) —CON(R)$_2$,
14) —CN,
15) —CO$_2$ C$_{1-6}$alkyl
16) benzoyl, either unsubstituted or substituted with C$_{1-6}$alkyl, C$_{1-6}$alkoxy, halo such as Cl, Br, F, or I, or hydroxy
17) —NRCOO(C$_{1-6}$alkyl),
18) —NRCOO phenyl either unsubstituted or substituted with C$_{1-6}$alkyl, C$_{1-6}$alkoxy, hydroxy or halo such as Cl, F, Br, or I,
19) —NR CON(R)$_2$,
20) —S(O)$_n$C$_{1-6}$alkyl,
21) —S(O)$_n$phenyl, either unsubstituted or substituted with C$_{1-6}$alkyl, C$_{1-6}$alkoxy, hydroxy, or halo such as F, Cl, Br, or I,
22) —CF$_3$,
23) —phenyl, either unsubstituted or substituted with C$_{1-6}$alkyl, C$_{1-6}$alkoxy, halo such as Cl, Br, F, or I, or hydroxy,
24) imidazolyl, or
25) —SO$_2$ N(R)$_2$, R$^2$ and R$^3$ taken together may be methylenedioxy or ethylenedioxy.

One embodiment of the novel compounds of this invention comprises those compounds wherein Q represents a 5-7 membered heterocycle and has the subgeneric structure

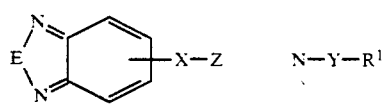

wherein Z is

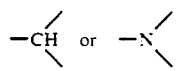

especially wherein Q represents piperazine or piperidine.

Another embodiment of the novel compounds of this invention is that wherein Q is —N(R)—, especially wherein R is hydrogen or C$_{1-6}$alkyl, preferably methyl.

It is preferred that X be —CO—, —CONR—(CH$_2$)$_m$—, or —(CH$_2$)$_m$— and that Y be —(CH$_2$)$_m$O— or —(CH$_2$)$_m$—.

It is also preferred that R$^1$ be

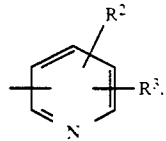  1)

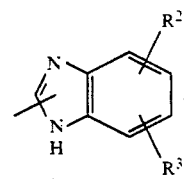  2)

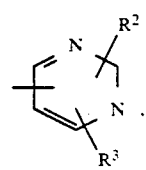  3)

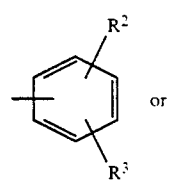  4)

or

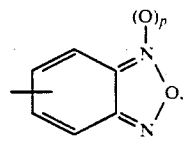  5)

especially 4-methanesulfonamidophenyl, benzofurazan-5-yl, pyridyl or benzofurazan-N-oxide-5(or 6)-yl.

The term "alkyl", if the number of carbons is unspecified, means C$_{1-6}$alkyl and "alkyl" of three or more carbon atoms includes straight chain, branched chain and cycloalkyl.

Also included within the scope of the present invention are the non-toxic pharmaceutically acceptable salts of the novel compounds. Acid addition salts are formed by mixing a solution of the compound with a solution of a pharmaceutically acceptable non-toxic acid such as hydrochloric acid, fumaric acid, maleic acid, succinic acid, acetic acid, citric acid, tartaric acid, phosphoric acid, or the like.

Also included within the scope of this invention are diastereomers and enantiomers of the novel compounds and mixtures thereof.

There are various processes for preparing the novel compounds of this invention. Most of the last-step processes, however, are acid condensations between an amine and a compound with a leaving group such as halo, mesyloxy, tosyloxy or benzenesulfonyloxy. Chemical representations of these processes are as follows:

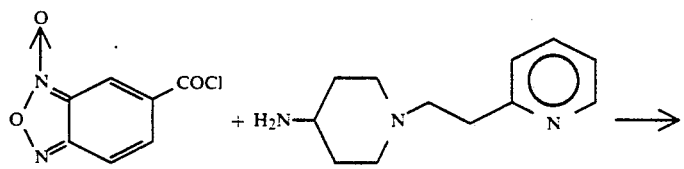  I

-continued
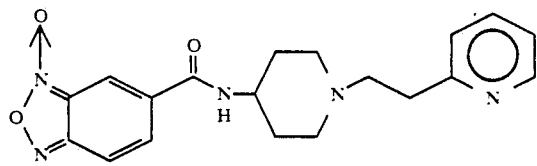
II
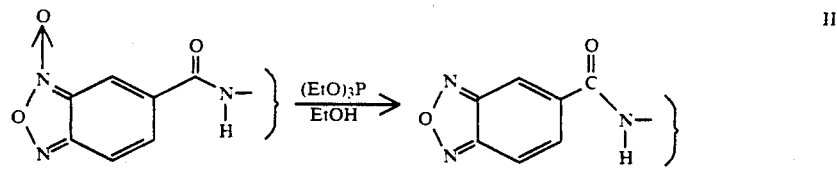
III
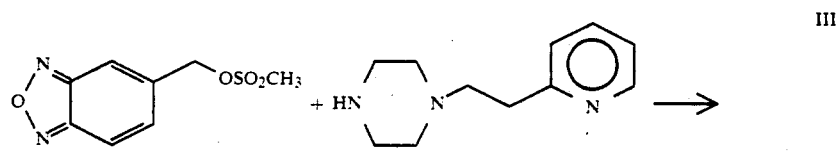
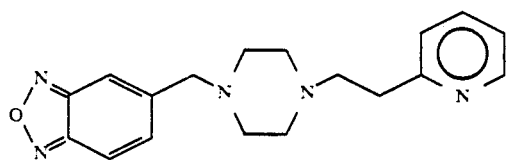
IV
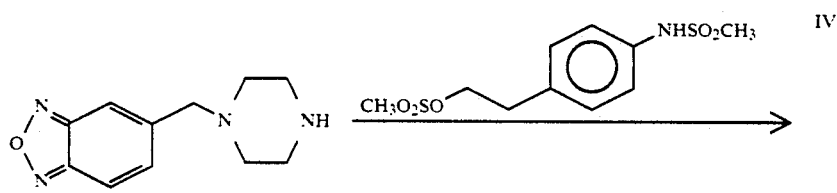
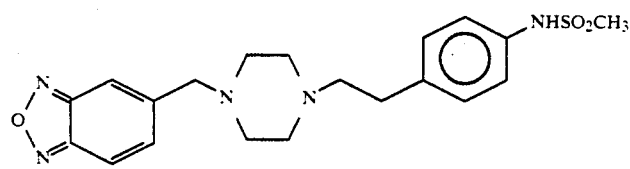
V
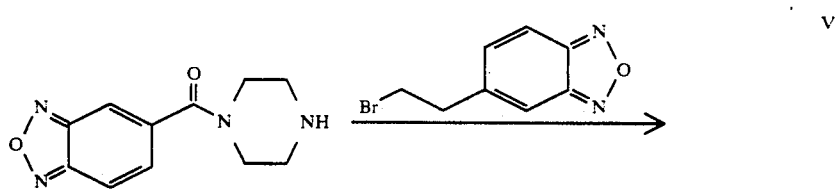
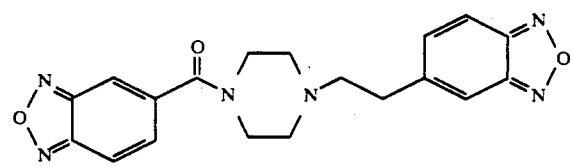
VI
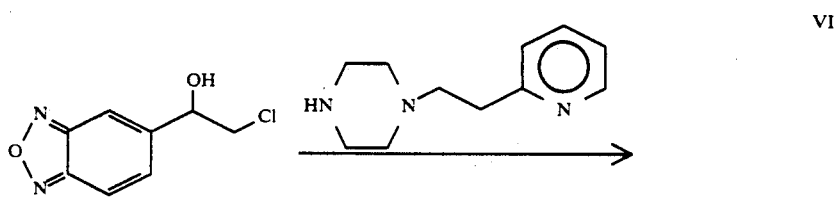

-continued

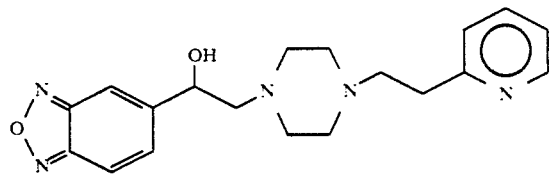

Reaction Scheme I demonstrates a general procedure for the preparation of compounds wherein X includes —CONH and comprises condensing a carboxylic acid halide such as the chloride with an amino compound in an inert organic solvent such as methylene chloride, THF, toluene, or the like at about −10° C. to +10° C. for about 15 minutes to 2 hours. The same reaction conditions pertain whether the amino compound presents an —NH₂ group or a piperazine type of nitrogen.

Reaction Scheme II portrays the reduction of benzofuroxan to benzofurazan with triethyl phosphite which proceeds at reflux temperature in ethanol over a period of 0.5 to 2 hours.

In reaction Scheme III and IV the leaving groups are methanesulfonyloxy. The reaction is conducted in an inert solvent such as methylene chloride at about 15° to 30° C. for about 18 to 36 hours.

Process V is similar to that of III and IV, except that the leaving group is bromo. For solubility reasons, the reaction is conducted in a solvent such as DMF at about 15° to 30° C. for about 18 to 36 hours, followed by heating at about 60° to 100° for about 2 to 8 hours if necessary to complete the reaction.

Process Scheme VI is similar to the other condensation reactions and is conducted in a lower alkanol in the presence of an acid acceptor such as sodium carbonate or bicarbonate, pyridine etc, at about 70°–90° C. for about 2 to 6 hours.

The compounds of the present invention have the pharmacological properties required for the antiarrhythmic agents of Class III, namely the prolongation of the myocardial action potential in vitro without a significant depression of the Vmax and with the prolongation of QTc-interval in anesthetized dogs. Moreover, the effects of many of the novel compounds are much more potent than the reference drug, sotalol.

The compounds of the present invention are effective in treating and preventing all types of arrhythmias including ventricular and atrial (supraventricular) arrhythmias. The compounds of the present invention are especially useful to control reentrant arrhythmias and prevent sudden death due to the ventricular fibrillation.

In the novel method of this invention of treating arrhythmia, a novel compound or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

The novel compounds of this invention can be administered as the sole active ingredient or in combination with other antiarrhythmic agents or other cardiovascular agents.

The compounds, or pharmaceutically acceptable salts thereof, of the present invention, in the described dosages, are adminstered orally, intraperitoneally, subcutaneously, intramuscularly, transdermally, sublingually or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

EXAMPLE 1

4-[N-(Benzofurazan-N-oxide-5(or 6)-carbonyl)aminomethyl]-1-[2-(2-pyridyl)ethyl]piperidine To a suspension of benzofurazan-N-oxide-5(or 6)-carboxylic acid (0.5 g, 2.8 mmol) in methylene chloride (10 ml) was added dimethylformamide (1 drop) followed by dropwise addition of oxalyl chloride (0.27 ml, 3.1 mmol). The resulting solution was stirred at room temperature for 3 hours, and then concentrated under reduced pressure. The yellow oil was redissolved in methylene chloride (10 ml), and was added to a cooled (0° C.) solution of 4-(aminomethyl)-1-(2-pyridylethyl)-piperidine (0.64 g, 2.9 mmol) in methylene chloride (5 ml). The reaction mixture was stirred at 0° C. for ½ hour. Solvent evaporation and flash chromatography (silica gel, chloroform-methanol-ammonium hydroxide 95/5/½) gave a foam (0.55 g, 50%); trituration with hexane-ethyl acetate gave 4-[N-(benzofurazan-N-oxide-5(or 6)-carbonyl)aminomethyl]-1-[2-(2-pyridyl)ethyl]-piperidine;

mp 142°–144° C.

Anal. Calc'd. for $C_{20}H_{23}N_5O_3$: C, 62.96; H, 6.09; N, 18.36. Found: C, 62.85; H, 6.15; N, 18.14.

Following the procedure substantially as described in Example 1, but employing the appropriate starting materials described in Table I, there were prepared the benzofurazan-N-oxide compounds also described in Table I wherein X is >C=O.

TABLE I

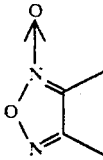

| X—Q—Y—R[1] | m.p. (°C.) | C | H | N |
|---|---|---|---|---|
| [−N(CH3)−CH2CH2−N(CH3)−CH2CH2−C6H4−NO2 (para)] | 116–118 | 56.09 / 56.27 | 4.98 / 4.85 | 18.17 / 18.08 |
| [−N(piperazine)−4-pyridyl] | 156–160 (dec.) | 59.06 / 59.35 | 4.66 / 4.63 | 21.53 / 21.74 |
| [−N(CH3)−CH2CH2−(2-pyridyl)] · ¼ H2O | 112–114 | 59.49 / 59.53 | 4.83 / 4.67 | 18.50 / 18.32 |
| [−N(piperazine)−CH2−C6H4−NO2 (para)] · ¾ H2O | 201–202 | 54.46 / 54.44 | 4.71 / 4.36 | 17.65 / 17.32 |
| [−N(piperazine)−(2-pyrimidinyl)] · ¼ H2O[1] | 167–169 | 54.45 / 54.42 | 4.42 / 4.17 | 25.41 / 25.29 |
| [−N(piperazine)−CH2CH2−(2-pyridyl)] · HCl[1] | 183–185 | 55.45 / 55.61 | 5.18 / 5.05 | 17.97 / 18.16 |
| [−NH−CH2CH2−N(Et)2] · HCl | 188–189 | 49.61 / 49.24 | 6.08 / 5.99 | 17.80 / 17.77 |

[1] diisopropylethylamine was added to the methylene chloride solvent.

EXAMPLE 2

1-(Benzofurazan-5-carbonyl)-4-(4-pyridyl)piperazine

A solution of 1-(benzofurazan-N-oxide-5(or 6)-carbonyl)-4-(4-pyridyl)piperazine (75 mg, 0.23 mmol) and triethyl phosphite (0.09 ml, 0.46 mmol) in ethanol (3.5 ml) was heated at reflux temperature for 1 hour. Solvent evaporation, flash chromatography (silica gel, chloroform-methanol-ammonium hydroxide 96/4/0.4), and trituration with hexane gave 1-(benzofurazan-5-carbonyl)-4-(4-pyridyl)piperazine (35 mg, 49%); mp 164°–166° C.

Anal. Calc'd. for $C_{16}H_{15}N_5O_2$: C, 62.12; H, 4.90; N, 22.64. Found: C, 61.80; H, 4.88; N, 22.28.

Following the procedure substantially as described in Example 2, but employing the appropriate starting materials described in Table II, there are produced the benzofurazan compounds also described in Table II wherein X is $>C=O$.

TABLE II

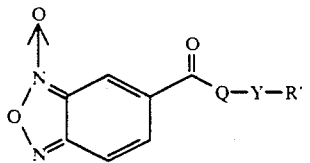

| X—Q—Y—R[1] | m.p. (°C.) | Analysis (calc/found) C | N |
|---|---|---|---|
| 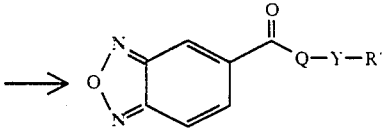 | 188–190 | 57.65  5.64<br>57.32  5.35 | 18.18<br>18.43 |
| 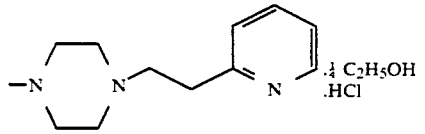 | 156–158 | 64.45  6.45<br>64.56  6.30 | 18.80<br>18.43 |
| 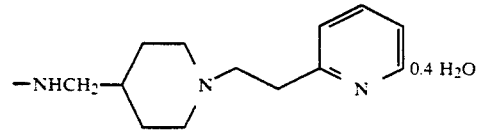 | 207–208 | 58.13  4.75<br>58.20  4.71 | 18.84<br>18.56 |
| 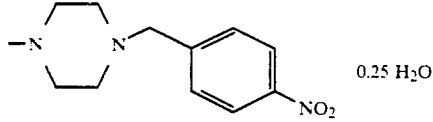 | 80–82 | 63.81  5.01<br>63.72  4.95 | 19.85<br>19.81 |
| 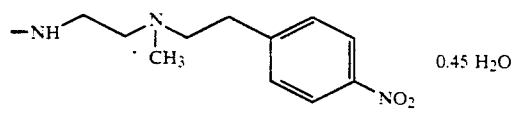 | 94–96 | 57.27  5.31<br>56.96  4.91 | 18.55<br>18.41 |
| 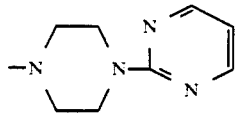 | 179–181 | 58.05  4.56<br>57.86  4.41 | 27.08<br>26.96 |
| 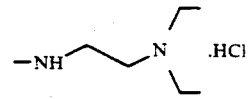 | 143–144 | 52.26  6.41<br>52.10  6.47 | 18.75<br>18.35 |

EXAMPLE 3

4-[N-(Benzofurazan-5-carbonyl)aminomethyl]-1-[2-(2-pyridyl)ethyl]piperidine

To a suspension of benzofurazan-5-carboxylic acid (150 mg, 0.91 mmol) in methylene chloride (3.3 ml) was added dimethylformamide (1 drop) followed by dropwise addition of oxalyl chloride (89 μl, 1.0 mmol). The resulting solution was stirred at room temperature for 3 hours and then concentrated under reduced pressure. The brown oil was redissolved in methylene chloride (3.3 ml) and was added to a cooled (0° C.) solution of 4-(aminomethyl)-1-(2-pyridylethyl)piperidine (0.21 g, 0.95 mmol) in methylene chloride (1.6 ml). The reaction mixture was stirred at 0° C. for 1½ hours. Solvent evaporation, flash chromatography (silica gel, chloroform-methanol-ammonium hydroxide, 95/5/½) and trituration with hexane-ethyl acetate gave 4-[N-(benzofurazan-5-carbonyl)aminomethyl]-1-(2-pyridylethyl)piperidine (133 mg, 40%);

mp 149°–151° C.

Anal. Calc'd. for $C_{20}H_{23}N_5O_2$: C, 65.72; H, 6.36; N, 19.17. Found: C, 65.66; H, 6.35; N, 18.98.

Employing the procedure substantially as described in Example 3, but substituting the appropriate starting materials depicted in Table III, there are produced the benzofurazan compounds also described in Table III wherein X is >C=O.

TABLE III

| X—Q—Y—R¹ | m.p. (°C.) | Analysis (Calc/Found) | | |
|---|---|---|---|---|
| | | C | H | N |
| -N(piperazine)N-CH₂CH₂-C₆H₄-NO₂ (4-nitro) | 141–143 | 59.82<br>59.83 | 5.03<br>4.95 | 18.36<br>18.40 |
| -NH-CH₂-(benzimidazol-2-yl) · HCl·0.5 H₂O | >265 | 53.18<br>52.91 | 3.88<br>3.52 | 20.68<br>20.41 |
| -N(homopiperazine)N-CH₂CH₂-C₆H₄-NO₂ · HCl·½ H₂O | 195–199 | 54.85<br>54.77 | 5.23<br>5.00 | 16.00<br>15.96 |
| -N(piperazine)N-CH₂CH₂-C₆H₅ · HCl | 237–239 | 61.19<br>60.97 | 5.69<br>5.70 | 15.03<br>14.91 |

EXAMPLE 4

1-(Benzofurazan-5-carbonyl)-4-[2-(benzofurazan-5-yl)ethyl]piperazine

Step A: Preparation of 1-[2-benzofurazan-5-yl-ethyl]piperazine

5-[2-(Methanesulfonyloxy)ethyl]]benzofurazan (242 mg, 1 mmol) and piperazine (0.86 g, 10 mmol) in DMF (9 ml) were stirred together at room temperature for 19 hours. The solvent was evaporated under reduced pressure and the residue was purified by flash column chromatography on silica gel eluting with CH₂Cl₂/CH₃OH/NH₃(Aq.); 90:10:1 to give the piperazine as a yellow solid (225 mg, 97%).

δH(CDCl₃) 7.75 (1H, d, J 9.2 Hz), 7.61 (1H,s) 7.31 (1H, d, J 9.2 Hz), 2.9 (6H, m), 2.67 (2H, t, J 7.6 Hz), 2.5 (4H, br s), and 1.7 (1H, br s).

Step B: Preparation of 1-(benzofurazan-5-carbonyl)-4-[2-(benzofurazan-5-yl)ethyl]piperazine Prepared by the procedure described in Example 3; m.p. 133°–135° C.

Anal. Calc'd. for C₁₉H₁₈N₆O₃: C, 60.31; H, 4.79; N, 22.21. Found: C, 59.96; H, 4.66; N, 22.03.

EXAMPLE 5

1-(Benzofurazan-5-carbonyl)-4-[2-(4-methanesulfonamidophenyl)ethyl]piperazine

Step A: Preparation of 1-[2-(4-methanesulfonamidophenyl)ethyl]piperazine

A solution of 4-[2-(4-methanesulfonyloxy)ethyl]methanesulfonanilide (1.5 g, 5.1 mmol) and piperazine (4.4 g, 51 mmol) in dimethylformamide (58 ml) was stirred at room temperature for 24 hours. Solvent evaporation and flash chromatography (silica gel, chloroform-methanol-ammonium hydroxide, 90/10/1) gave 1-[2-(4-methanesulfonamidophenyl)ethyl]piperazine (1.2 g, 86%); ¹H NMR (CDCl₃) δ2.53 (m,8H), 2.78 (m,2H), 2.93 (m,7H), 7.19 (dd,4H).

Step B: Preparation of 1-(benzofurazan-5-carbonyl)-4-[2-(4-methanesulfonamido-phenyl)ethyl]piperazine Prepared by the process of Example 3 except that dimethylformamide was substituted for methylene chloride.

mp 163°–165° C.

Anal. Calc'd. for C₂₀H₂₃N₅O₄S: C, 55.92; H, 5.41; N, 16.31. Found: C, 55.99; H, 5.33; N, 16.33.

EXAMPLE 6

4-(Benzofurazan-5-methyl)-1-(4-pyridyl)piperazine

Step A: Preparation of 5-(methanesulfonyloxymethyl)benzofurazan

5-Benzofurazanmethanol (0.6 g, 4 mmol) and triethylamine (0.84 mmol, 0.61 g, 6 mmol) were dissolved in dichloromethane (20 ml) and cooled to −20° C. Methanesulfonyl chloride (0.37 ml, 0.55 g, 4.8 mmol) was added dropwise and the mixture was stirred at −20° C. for 20 minutes, diluted with dichloromethane (30 ml), washed with water (30 ml), dried (Na₂SO₄), and evaporated under reduced pressure to give the benzofurazan as a white solid (0.91 g, 99%).

δH(CDCl₃) 7.95 (1H, d, J 9.2 Hz), 7.93 (1H, s), 7.46 (1H, d, J 9.2 Hz), 5.35 (2H, s), and 3.14 (3H, s).

Step B: Preparation of 4-(Benzofurazan-5-methyl)-1-(4-pyridyl)piperazine 5-(Methanesulfonyloxymethyl) benzofurazan (137 mg, 0.6 mmol) and 1-(4-pyridyl)piperazine (147 mg, 0.9 mmol) in dichloromethane (2 ml) was stirred at room temperature for 24 hours. The solvent was evaporated under reduced pressure and the residue was purified by flash column chromatography on silica gel, eluting with CH₂Cl₂/MeOH/NH₃(Aq.); 95:5:1, to give a white solid (44 mg, 25%), which was recrystallized from ethyl acetate/hexane to give the piperazine as needles, mp. 119°–120° C.

δH(CDCl$_3$) 8.31 (2H, dd, J 5.1, 1.5 Hz), 7.83 (1H, d, J 9.3 Hz), 7.76 (1H, s), 7.55 (1H, d, J 9.3 Hz), 6.69 (2H, dd, J 5.1, 1.5 Hz), 3.66 (2H, s) 3.39 (4H, t, J 5.1 Hz) and 2.65 (4H, t, J 5.1 Hz).

Elemental analysis for C$_{16}$H$_{17}$N$_5$O:

Calculated: C, 65.07; H, 5.80; N, 23.71%. Found: C, 64.84; H, 5.95; N, 23.55%.

EXAMPLE 7

1-(Benzofurazan-5-methyl)-4-[2-(2-pyridyl)ethyl]piperazine

Employing the procedure substantially as described in Example 6, Step B, 5-(methanesulfonyloxymethyl)-benzofurazan (91 mg, 0.4 mmol), 1-[2-(2-pyridyl)ethyl]piperazine (141 mg, 0.6 mmol) and diisopropylethylamine (0.35 ml, 0.26 g, 2 mmol) in DMF (1.5 ml) gave, after purification by flash column chromatography on silica gel, eluting with CH$_2$Cl$_2$/MeOH/NH$_3$(Aq); 92:8:0.8, and recrystallization from ethyl acetate/hexane, the piperazine as yellow needles (80 mg, 62%), mp 79°–80° C.

δH(CDCl$_3$) 8.53 (1H, br d, J 4.7 Hz), 7.77 (1H, d, J 9.2 Hz), 7.70 (1H, s), 7.60 (1H, dt, Jd 1.7, Jt 7.6 Hz), 7.50 (1H, d, J 9.2 Hz), 7.19 (1H, d, J 7.6 Hz), 7.12 (1H, dd, J 7.6, 4.7 Hz) 3.58 (2H, s), 3.00 (2H, m), 2.79 (2H, m), and 2.56 (8H, br, s).

Elemental analysis for C$_{18}$H$_{21}$N$_5$O:

Calculated: C, 66.85; H, 6.54; N, 21.66%. Found: C, 66.92; H, 6.49; N, 21.66%.

EXAMPLE 8

1-(Benzofurazan-5-methyl)-4-[2-(4-nitrophenyl)ethyl]-piperazine

Employing the procedure substantially as described in Example 6, Step B, 5-(methanesulfonyloxymethyl)-benzofurazan (91 mg, 0.4 mmol), 1-[2-(4-nitrophenyl)ethyl]piperazine (141 mg, 0.6 mmol) and diisopropylethylamine (0.35 ml, 0.26 g, 2 mmol) in DMF (1.5 ml) gave, after purification by flash column chromatography on silica gel, eluting with CH$_2$Cl$_2$/MeOH/NH$_3$(Aq); 98:2:0.2, and recrystallization from ethyl acetate/hexane, the piperazine as yellow needles (91 mg, 62%), mp 99°–101° C.

δH(CDCl$_3$) 8.15 (2H, d, J 8.7 Hz), 7.77 (1H, d, J 9.3 Hz), 7.71 (1H, s), 7.49 (1H, d, J 9.3 Hz), 7.37 (2H, d, J 8.7 Hz), 3.59 (2H,s) 2.91 (2H, t, J 7.8 Hz) 2.65 (2H, t, J 7.8 Hz), and 2.56 (8H, br, s).

Elemental analysis for C$_{19}$H$_{21}$N$_5$O$_3$:

Calculated: C, 62.11; H, 5.76; N, 19.06%. Found: C, 62.25; H, 5.88; N, 19.10%.

EXAMPLE 9

1-(Benzofurazan-5-methyl)-4-[2-(4-methanesulfonamidophenyl)ethyl]piperazine dihydrochloride Employing the procedure substantially as described in Example 6, Step B, 5-(methane-sulfonyloxymethyl)-benzofurazan (91 mg, 0.4 mmol), 1-[2-(4-methanesulfonamidophenyl)ethyl]piperazine (170 mg, 0.6 mmol) and diisopropylethylamine (0.35 ml, 0.26 g, 2 mmol) in DMF (2.5 ml) gave, after purification by flash column chromatography on silica gel, eluting with CH$_2$Cl$_2$/MeOH/NH$_3$(Aq); 95:5:0.5, a white solid which was dissolved in THF (5 ml) and treated with ethanolic HCl (Ca. 1M, 3 ml). The solid was collected and dried in vacuo to give the dihydrochloride as a white solid (127 mg, 65%). mp >250° C.

δH(DMSO) 9.70 (1H, s), 8.25 (1H, br s), 8.11 (1H, d, J 9.1 Hz), 7.80 (1H, br d, J 9.1 Hz), 7.22 (2H, d, J 8.5 Hz), 7.15 (2H, d, J 8.5 Hz), 4.4–3.0 (16H, m), and 2.93 (3H, s).

Elemental analysis for C$_{20}$H$_{25}$N$_5$O$_3$S.2HCl

Calculated: C, 49.18; H, 5.57; N, 14.34%. Found: C, 48.99; H, 5.50; N, 14.16%.

EXAMPLE 10

1-(Benzofurazan-5-methyl)-4-[2-(4-methanesulfonamidophenyl)ethyl]piperazine

Step A: Preparation of 1-(Benzofurazan-5-methyl)piperazine

Employing the procedure substantially as described in Example 6, Step B, 5-(methanesulfonyloxymethyl)-benzofurazan (228 mg, 1 mmol) and piperazine (0.86 g, 10 mmol) in DMF (5 ml) gave, after purification by flash column chromatography on silica gel, eluting with CH$_2$Cl$_2$/MeOH/NH$_3$(Aq); 90:10:1, the piperazine as a yellow oil (197 mg, 90%).

δH(CDCl$_3$) 7.77 (1H, d, J 9.0 Hz), 7.70 (1H, s), 7.50 (1H, d, J 9.0 Hz), 3.55 (2H, s), 2.92 (4H, t, J 4.9 Hz), 2.47 (4H, br s), and 1.72 (1H, br s).

Step B: Preparation of 1-(Benzofurazan-5-methyl)-4-[2-(4-methanesulfonamidophenyl)ethyl]piperazine 1-(Benzofurazan-5-methyl)piperazine (87 mg, 0.4 mmol) was dissolved in DMF (2 ml) and 4-[2-(4-methanesulfonyloxy)ethyl]methanesulfonanilide (117 mg, 0.4 mmol) was added. The mixture was stirred at room temperature for 24 hours, then at 80° C. for 5 hours, cooled and the solvent was evaporated under reduced pressure. The residue was purified by flash column chromatography on silica gel, eluting with CH$_2$Cl$_2$/CH$_3$OH/NH$_3$(Aq); 95:5:0.5, and crystallized from ethyl acetate/hexane to give the piperazine as needles (53 mg, 32%), mp 164°–165° C.

δH(CDCl$_3$) 7.78 (1H, d, J 9.3 Hz), 7.72 (1H, s), 7.49 (1H, d, J 9.3 Hz), 7.20, 7.14 (Each 2H, ABq, J 8.4 Hz), 6.38 (1H, br s) 3.59 (2H, s), 2.99 (3H,s) 2.79 (2H, m), and 2.6 (10H, m).

Elemental analysis for C$_{20}$H$_{25}$N$_5$O$_3$S:

Calculated: C, 57.81; H, 6.06; N, 16.85%. Found: C, 57.55; H, 5.90; N, 16.69%.

EXAMPLE 11

4-[2-(Benzofurazan-5-yl)ethyl]-1-(benzofurazan-5-methyl)piperazine

Step A: Preparation of 5(or 6)-(2-Hydroxyethyl)benzofurazan-N-oxide 4-(2-Acetoxyethyl)-2-nitroacetanilide (4.16 g, 15.6 mmol) was dissolved in methanol (25 ml) and methanolic potassium hydroxide (20%, 25 ml) was added dropwise. The mixture was stirred at room temperature for 40 minutes, then cooled in ice. Aqueous sodium hypochlorite (Ca. 5%, 50 ml) was added dropwise over 30 minutes with vigorous stirring Water (50 ml) was added and the mixture was extracted with dichloromethane (3×100 ml). The combined organic fractions were dried (Na$_2$SO$_4$) and evaporated under reduced pressure to give the benzofurazan-N-oxide as a yellow oil (2.76 g, 98%).

δH(CDCl$_3$) 7.6–7.1 (3H, br m), 3.95 (2H, t, J 6.2 Hz), 2.91 (2H, t, J 6.2 Hz), and 2.1 (1H, br s).

Step B: Preparation of 5-(2-hydroxyethyl)benzofurazan

5(or 6)-(2-Hydroxyethyl)benzofurazan-N-oxide (2.23 g, 12.4 mmol) was dissolved in methanol (25 ml) and trimethylphosphite (4.38 ml, 4.60 g, 37.1 mmol) was added. The mixture was heated under reflux for 3 hours, cooled and the solvent was evaporated under reduced pressure. The residue was purified by flash column chromatography on silica gel eluting with ether to give the benzofurazan as a yellow oil (1.52 g, 75%).

δH(CDCl$_3$) 7.78 (1H, d, J 9.2 Hz)7.65 (1H, s), 7.34 (1H, d, J 9.2 Hz), 3.98 (2H, t, J 6.3 Hz), 2.98 (2H, t, J 6.3 Hz), and 1.9 (1H, br s).

Step C: Preparation of 5-[2-(methanesulfonyloxy)ethyl]benzofurazan 5-(2-Hydroxyethyl)benzofurazan (1.48 g, 9 mmol) was dissolved in dichloromethane (45 ml) and triethylamine (1.88 ml, 1.37 g, 13.5 mmol) was added. The mixture was cooled to −30° C. and methanesulfonyl chloride (0.84 ml, 1.24 g, 10.8 mmol) was added dropwise over 5 minutes. The mixture was stirred at −30° C. for 15 minutes and dichloromethane (100 ml) was added. The mixture was washed with water (100 ml), dried (Na$_2$SO$_4$) and evaporated under reduced pressure to give the benzofurazan as a yellow solid (2.10 g, 96%).

δH(CDCl$_3$) 7.83 (1H, d, J 9.5 Hz), 7.70 (1H,s) 7.32 (1H, d, J 9.5 Hz), 4.53 (2H, t, J 6.4 Hz), 3.19 (2H, t, J 6.4 Hz), and 2.99 (3H,s).

Step D: Preparation of 4-[2-(Benzofurazan-5-yl)ethyl]-1-(benzofurazan-5-methyl)piperazine:

1-(Benzofurazan-5-methyl)-piperazine (87 mg, 0.4 mmol) and 5-[2-(methanesulfonyloxy)ethyl]benzofurazan (97 mg, 0.4 mmol) in DMF (2 ml) were stirred together at room temperature for 19 hours and at 80° C. for 5 hours. The solvent was evaporated under reduced pressure and the residue was purified by flash column chromatography on silica gel eluting with CH$_2$Cl$_2$/CH$_3$OH/NH$_3$(Aq.); 98:2:0.2, and trituration with hexane/ethyl acetate to give the piperazine as a yellow solid (22 mg, 15%), mp 80°–82° C.

δH(CDCl$_3$) 7.78, 7.76 (Each 1H, d, J 9.3 Hz), 7.72, 7.64 (Each 1H,s), 7.49, 7.30 (Each 1H, d, J 9.3 Hz), 3.59 (2H,s), 2.91, 2.70 (Each 2H, t, J 7.5 Hz), and 2.57 (8H, br s).

Elementary analysis for C$_{19}$H$_{20}$N$_6$O$_2$.0.4 H$_2$O:
Calculated: C, 61.41; H, 5.64; N, 22.61%. Found: C, 61.62; H, 5.35; N, 22.48%.

EXAMPLE 12

1-(4-Methanesulfonamidophenoxy)-2-{N-[2-(benzofurazan-5-yl)ethyl]-N-methylamino}ethane hydrochloride

Step A: Preparation of 5-(2-bromoethyl) benzofurazan

A solution of 5-(2-hydroxyethyl) benzofurazan (1.0 g, 6.1 mmol) and carbon tetrabromide (2.6 g, 7.9 mmol) in methylene chloride (10 ml) was cooled to 0° C. A solution of triphenylphosphine (1.9 g, 7.3 mmol) in methylene chloride (10 ml) was added dropwise and the reaction was stirred for 5 minutes. Solvent evaporation and flash chromatography (silica gel, ethyl acetate-hexane, 5/95) gave 5-(2-bromoethyl)benzofurazan (1.2 g, 86%);

$^1$H NMR (CDCl$_3$) δ3.32(t,2H), 3.69(t,2H), 7.32(d,1H), 7.69(s,1H), 7.84(d,1H).

Step B: Preparation of 1-(4-methanesulfonamidophenoxy)-2-{N-[2-(benzofurazan-5-yl)ethyl]-N-methylamino}ethane hydrochloride 4-[2-(Methylaminoethoxy)]methanesulfonanilide hydrobromide, (325 mg, 1 mmol), 5-(2-bromoethyl)benzofurazan (568 mg, 2.5 mmol), sodium bicarbonate (336 mg, 4 mmol) and lithium iodide (3 mg) in ethanol (10 ml) were heated under reflux for 19 hours, cooled and the solvent was evaporated under reduced pressure. The residue was purified by flash column chromatography on silica gel eluting with CH$_2$Cl$_2$/CH$_3$OH/NH$_3$(Aq.); 96:4:0.4 to give a yellow gum which was dissolved in ethanol (3 ml) and treated with ethanolic HCl (Ca. 1M, 3 ml). The solvent was evaporated under reduced pressure and the residue was crystallized from ethanol/hexane to give the hydrochloride as needles (210 mg, 49%), mp 181°–183° C.

δH(CDCl$_3$) 10.7 (1H, br s), 9.46, (1H, s), 8.07, (1H, d, J 9.3 Hz), 7.95 (1H, s), 7.58, (1H, d, J 9.3 Hz), 7.18 (2H, d J 9.0 Hz), 6.99 (2H, d, J 9.0 Hz), 4.38 (2H, br t, J 4.8 Hz), 3.7–3.2 (6H, m), 2.92 (3H, br s), and 2.89 (3H, s).

Elemental analysis for C$_{18}$H$_{22}$N$_4$O$_4$S.HCl:
Calculated: C, 50.64; H, 5.43; N, 13.12%. Found: C, 50.70; H, 5.38; N, 12.98%.

EXAMPLE 13

1-[2-(6-Methyl-2-pyridyl)ethyl]-4-(benzofurazan-5-carbonyl)piperidine dihydrochloride

Step A: Preparation of 1-Benzoyl-4-(4-acetamidobenzoyl)piperidine

N-Benzoylisonipecotic acid (11.65 g, 50 mmol) was dissolved in dichloromethane (150 ml) and dimethylformamide (1 ml) was added. Oxalyl chloride (4.80 ml, 6.98 g, 55 mmol) was added dropwise and the mixture was stirred for 3 hours. The solvent was evaporated under reduced pressure to give a yellow oil which crystallized slowly. The residue was dissolved in chloroform (25 ml) and was added to a stirred suspension of acetanilide (13.52 g, 0.1 mol) in 1,2,4-trichlorobenzene (150 ml). The mixture was heated to 60° C. and aluminum chloride (26.7 g, 0.2 mmol) was added in portions over 15 minutes. The dark mixture was heated to 100° C. for 90 minutes, cooled and water (150 ml) was added slowly. The mixture was extracted with dichloromethane (4×150 ml) and the combined organic fractions were washed with water (200 ml), dried (Na$_2$SO$_4$) and evaporated under reduced pressure to give a purple oil. The compound was purified by flash column chromatography on silica gel eluting with ethyl acetate/3% CH$_3$OH to give the piperidine as a pale yellow solid (9.19 g, 52%).

δH(CDCl$_3$) 7.92 (2H, d, J 8.3 Hz), 7.72 (1H, br s), 7.64 (2H, d, J 8.3 Hz), 7.41 (5H, s), 4.7 (1H, br s), 3.9 (1H, br s), 3.5 (1H, br m), 3.1 (2H, br s), 2.19 (3H, s), and 2.1–1.7 (4H, br m).

Step B: Preparation of 1-Benzoyl-4[(4-acetamidophenyl)hydroxymethyl]-piperidine Sodium borohydride (1.13 g, 30 mmol) was added to a stirred suspension of 1-benzoyl-4-(4-acetamidobenzoyl)piperidine (10.0 g, 29 mmol) in ethanol (300 ml), cooled in a water bath. The mixture was stirred at room temperature for 1 hour then additional sodium borohydride (1.13 g, 30 mmol) was added and stirring was continued for 2 hours. The solvent was evaporated under reduced pressure and water (200 ml), HCl—H$_2$O (6M, 15 ml) and methanol (15 ml) were added. The mixture was extracted with dichloromethane (4×200 ml) and the combined organic fractions were dried (Na$_2$SO$_4$) and evaporated under reduced pressure to give an off-white solid which was crystallized from ethanol to give the piperidine as white crystals. (5.77 g, 57%)

δH(CDCl$_3$) 9.87 (1H, s), 7.50 (2H, d, J 8.3 Hz), 7.42 (3H, m), 7.33 (2H, m), 7.19 (2H, d J 8.3 Hz), 5.16 (1H, d, J 4.3 Hz), 4.5 (1H, br s), 4.2 (1H, m), 3.6 (1H, br s), 2.9 (1H, br s), 2.6 (1H, br s), 2.02 (3H, s), 1.7 (2H, br s), 1.3 (1H, br s), and 1.2 (2H, br s).

Step C: Preparation of 1-Benzoyl-4-[(benzofuroxan-5(or 6)-yl)hydroxymethyl]piperidine 4-Dimethylaminopyridine (195 mg, 1.6 mmol) was added to a stirred suspension of 1-benzoyl-4-[(4-acetamidophenyl)hydroxymethyl]piperidine (5.63 g, 16 mmol) in acetic anhydride (50 ml) and the mixture was stirred at room temperature for 24 hours. The mixture was cooled in ice and nitric acid (90%, 7.5 ml) was added dropwise. The mixture was stirred at 0° C. for 30 minutes, diluted with dichloromethane (200 ml), washed with aqueous sodium hydrogen carbonate (saturated, 250 ml), dried (Na$_2$SO$_4$) and evaporated under reduced pressure to give an orange foam. The foam dissolved in methanol (25 ml) and a solution of potassium hydroxide (5 g) in methanol (25 ml) was added dropwise with stirring and cooling. The mixture was stirred at room temperature for 30 minutes, cooled in ice and aqueous sodium hypochlorite (Ca. 5%, 50 ml) was added dropwise over 30 minutes. Water (50 ml) was added and the mixture was extracted with dichloromethane (3×100 ml). The combined organic fractions were dried (Na$_2$SO$_4$) and evaporated under reduced pressure to give the piperidine as an orange foam (5.61 g, 99%).

δH(CDCl$_3$) 7.6–7.2 (8H, br m), 4.8 (1H, br s), 4.49 (1H, d, J 6.2 Hz), 3.8 (1H, br s), 2.9 (1H, br s), 2.7 (1H, br s), 2.5 (1H, br s, exchanges with D$_2$O), and 2.0–1.3 (5H, br m).

Step D: Preparation of 1-Benzoyl-4-(benzofuroxan-5(or 6)-carbonyl)piperidine Dimethylsulfoxide (2.34 ml, 2.58 g, 33 mmol) in dichloromethane (7.5 ml) was added dropwise to a stirred solution of oxalyl chloride (1.44 ml, 2.09 g, 16.5 mmol) in dichloromethane (37.5 ml) cooled to −60° C. The mixture was stirred at −60° C. for 5 minutes and 1-benzoyl-4-[(benzofuroxan-5(or 6)-yl)hydroxymethyl]piperidine (5.30 g, 15 mmol) in dichloromethane (15 ml) was added dropwise. The mixture was stirred at −60° C. for 15 minutes then triethylamine (10.45 ml, 7.59 g, 75 mmol) was added dropwise. The mixture was stirred at −60° C. for 5 minutes then allowed to warm to room temperature and poured into water (75 ml). The layers were separated and the aqueous layer was extracted with dichloromethane (2×75 ml). The combined organic fractions were dried (Na$_2$SO$_4$) and evaporated under reduced pressure to give a dark solid which was purified by flash column chromatography on silica gel, eluting with ethyl acetate/50% hexane to give the piperidine as an orange solid (4.06 g, 77%).

δH(CDCl$_3$) 8.24 (1H, br s), 7.89 (1H, br s), 7.68 (1H, br s), 7.42 (5H, s), 4.75 (1H, br s), 3.9 (1H, br s), 3.55 (1H, br m), 3.1 (2H, br s), and 2.2–1.7 (4H, m).

Step E: Preparation of 4-(Benzofurazan-5-carbonyl)piperidine hydrochloride

Triethylphosphite (5.92 ml, 5.73 g, 34.5 mmol) was added to a stirred suspension of 1-benzoyl-4-(benzofuroxan-5(or 6)-carbonyl)piperidine (4.04 g, 11.5 mmol) in ethanol (50 ml) and the mixture was heated under reflux for 2 hours, cooled and the solvent was evaporated under reduced pressure. Methanol (60 ml) and aqueous HCl (6M, 90 ml) were added and the mixture was heated under reflux for 26 hours. The mixture was cooled and the solvent was evaporated under reduced pressure. Aqueous sodium hydrogen carbonate (saturated, 200 ml) and aqueous sodium hydroxide (20%, 20 ml) were added and the mixture was extracted with dichloromethane (8×100 ml). The combined organic fractions were dried (Na$_2$SO$_4$) and evaporated under reduced pressure. The residue was dissolved in ethanol (50 ml) and ethanolic HCl (Ca. 1M, 50 ml) was added dropwise. The mixture was cooled in ice and the solid was collected and dried in vacuo to give the hydrochloride as light brown crystals (2.18 g, 71%), mp >250° C.

δH(DMSO) 9.06 (1H, s), 9.0 (2H, br s), 8.20 (1H, d, J 9.3 Hz), 8.00 (1H, d, J 9.3 Hz), 3.96 (1H, m), 3.34 (2H, m), 3.06 (2H, m), 2.05 (2H, m), and 1.85 (2H, m).

Elemental analysis for C$_{12}$H$_{13}$N$_3$O$_2$.HCl.0.15 H$_2$O:
Calculated: C, 53.30; H, 5.33; N, 15.54%. Found: C, 53.24; H, 5.12; N, 15.53%.

Step F: Preparation of 1-[2-(6-Methyl-2-pyridyl)ethyl]-4-(benzofurazan-5-carbonyl)piperidine dihydrochloride 4-(Benzofurazan-5-carbonyl)piperidine hydrochloride (268 mg, 1 mmol), 2-methyl-6-vinylpyridine (286 mg, 2.4 mmol) and sodium acetate (187 mg, 2.3 mmol) in methanol/water (1:1, 4 ml) were heated under reflux for 3 hours, cooled and the solvent was evaporated under reduced pressure. The residue was purified by flash column chromatography on silica gel, eluting with CH$_2$Cl$_2$/CH$_3$OH/NH$_3$(Aq.); 96:4:0.4 to give a light brown solid. This was suspended in ethanol (2 ml) and ethanolic HCl (Ca. 1M, 2 ml) was added. The mixture was stirred at room temperature for 4 hours and the solid was collected and dried in vacuo to give the dihydrochloride as a light brown solid (260 mg, 61%), mp 228°–231° C.

δH(DMSO) 11.1 (1H, br s), 9.05 (1H, s), 8.25 (1H, br m), 8.19 (1H, d, J 9.5 Hz), 7.99 (1H, d, J 9.5 Hz), 7.65 (2H, br m), 4.0–3.1 (10H, m), 2.71 (3H, s), and 2.10 (4H, br m).

Elemental analysis for C$_{20}$H$_{22}$N$_4$O$_2$.2HCl:
Calculated: C, 56.74; H, 5.71; N, 13.23%. Found: C, 56.34; H, 5.80; N, 13.13%.

EXAMPLE 14

1-[2-(Benzofurazan-5-yl)ethyl]-4-(benzofurazan-5-carbonyl)piperidine hydrochloride 4-(Benzofurazan-5-carbonyl)piperidine hydrochloride (80 mg, 0.3 mmol), 5-(2-bromoethyl)benzofurazan (170 mg, 0.75 mmol), sodium bicarbonate (101 mg, 1.2 mmol) and lithium iodide (1 mg) in ethanol were heated under reflux for 19 hours, cooled and the solvent was evaporated under reduced pressure. The residue was purified by flash column chromatography on silica gel. eluting with $CH_2Cl_2/CH_3OH/NH_3(Aq.)$; 98:2:0.2 to give a yellow solid. This was dissolved in ethyl acetate (2 ml), and ethanolic HCl (Ca. 1M, 1 ml) was added. The resulting solid was collected and dried in vacuo to give the hydrochloride as a white solid (50 mg, 40%), mp 226°-228° C.

δH(DMSO) 10.5 (1H, br s), 9.05 (1H, s), 8.18 (1H, d, J 9.4 Hz), 8.09 (1H, d, J 9.4 Hz), 7.98 (1H, d, J 9.4 Hz), 7.96 (1H, s), 7.59 (1H, d, J 9.4 Hz), 4.0-3.0 (9H, m), and 2.2-1.8 (4H, m).

Elemental analysis for $C_{20}H_{20}ClN_5O_3$:

Calculated: C, 58.04; H, 4.87; N, 16.92%. Found: C, 57.78; H, 4.84; N, 16.92%.

EXAMPLE 15

1-[2-(4-Methanesulfonamidophenyl)ethyl]-4-(benzofurazan-5-carbonyl)piperidine hydrochloride In the manner described in Example 14, 4-(benzofurazan-5-carbonyl)piperidine hydrochloride (80 mg, 0.3 mmol), 4-[2-(methanesulfonyloxy)ethyl]methanesulfonanilide (220 mg, 0.75 mmol) and sodium bicarbonate (101 mg, 1.2 mmol) in ethanol (3 ml) heated at reflux for 19 hours gave, after purification by flash column chromatography on silica gel, eluting with $CH_2Cl_2/CH_3OH/NH_3(Aq.)$; 98:2:0.2, treatment with ethanolic HCl and trituration with methanol, the hydrochloride as a white solid (78 mg, 56%), mp >250° C.

δH(DMSO) 10.45 (1H, br s), 9.70 (1H, s), 9.04 (1H, s), 8.17 (1H, d, J 9.4 Hz), 7.96 (1H, d, J 9.4 Hz), 7.34-7.08 (4H, m), 4.0-2.9 (9H, m), 2.96 (3H, s), and 2.2-1.8 (4H, m).

Elemental analysis for $C_{21}H_{24}N_4O_4S.HCl.0.4 CH_3OH$:

Calculated: C, 53.80; H, 5.61; N, 11.73%. Found: C, 53.86; H, 5.24; N, 11.42%.

EXAMPLE 16

1-[2-(4-Nitrophenyl)ethyl]-4-(benzofurazan-5-carbonyl)piperidine hydrochloride

In the manner described in Example 14, 4-(benzofurazan-5-carbonyl)piperidine hydrochloride (80 mg, 0.3 mmol), 4-nitrophenethyl bromide (172 mg, 0.75 mmol), sodium bicarbonate (101 mg, 1.2 mmol), and lithium iodide (1 mg) in ethanol (3 ml) under reflux for 3 hours gave, after purification by flash column chromatography on silica gel, eluting with $CH_2Cl_2/CH_3OH/NH_3(Aq.)$; 96:4:0.4 and treatment with ethanolic HCl, the hydrochloride as a white solid (44 mg, 35%), mp 238°-240° C.

δH(DMSO) 10.7 (1H, br s), 9.03 (1H, s), 8.22 (2H, d, J 8.6 Hz), 8.16 (1H, d, J 9.5 Hz), 7.96 (1H, d, J 9.5 Hz), 7.59 (2H, d, J 8.6 Hz), 4.0-3.0 (9H, m), and 2.2-1.9 (4H, m).

Elemental analysis for $C_{20}H_{20}N_4O_4.HCl$:

Calculated: C, 57.63; H, 5.08; N, 13.44%. Found: C, 57.45; H, 4.96; N, 13.29%.

EXAMPLE 17

4-[2-(Benzofurazan-5-yl)ethyl]-1-(indole-5-carbonyl)-piperazine

Indole-5-carboxylic acid (57 mg, 0.35 mmol) was dissolved in THF (2 ml) and DMF (1 drop), then oxalyl chloride (37 μl, 54 mg, 0.42 mmol) was added. The mixture was stirred at room temperature for 3 hours, the solvent was evaporated under reduced pressure and the residue was dissolved in DMF (2 ml) and added to a stirred solution of 1-[2-(benzofurazan-5-yl)ethyl]piperazine (81 mg, 0.35 mmol) and diisopropylethylamine (91 μl, 68 mg, 0.52 mmol) in dichloromethane (1 ml). The mixture was stirred at room temperature for 24 hours, then the solvent was evaporated under reduced pressure. The residue was purified by flash column chromatography on silica gel, eluting with $CH_2Cl_2/CH_3OH/NH_3$; 96:4:0.4 and crystallized from ethyl acetate/$CHCl_3$/hexane to give the piperazine as yellow microcrystals (16 mg, 12%), mp 180°-183° C.

δH(CDCl$_3$) 8.34 (1H, br s), 7.76 (1H, d, J 9.4 Hz), 7.73 (1H, s), 7.62 (1H, s), 7.40 (1H, d, J 8.4 Hz), 7.31-7.26 (3H, m), 6.60 (1H, br s), 3.7 (4H, br s), 2.92 (2H, t, J 7.4 Hz), 2.72 (2H, t, J 7.4 Hz), and 2.6 (4H, br s).

EXAMPLE 18

(±)-1-[2-(Benzofurazan-5-yl)-2-hydroxyethyl]-4-[2-(2-pyridyl)ethyl]piperazine

Step A: Preparation of 5-[(2-chloro-1-oxo)ethyl]benzofurazan

To a solution of 0.84 g (5.0 mmoles) benzofurazan-5-carboxylic acid and 1 drop dimethylformamide in 20 ml methylene chloride cooled in an ice-bath was added 0.70 g (5.5 mmoles) oxalyl chloride. The solution was warmed to room temperature, stirred for 3 hours, and the solvent was removed in vacuo. The residual oil was extracted with 3×15 ml warm hexane. The combined extract was evaporated to dryness, the resulting solid was stirred under 2 ml cold hexane, the hexane was decanted, and the solid was dried to give 0.895 g (98%) crude benzofurazan-5-carbonyl chloride.

To a solution of approximately 0.63 g (approx. 15 moles) diazomethane in 30 ml ether cooled in a dry ice/acetone bath (−78° C.) was added dropwise a solution of 0.895 g (4.9 mmoles) 5-benzofurazon-5-carbonyl chloride in 10 ml ether. The mixture was stirred 40 minutes at −78°, then placed under vacuum for 5 minutes to remove excess diazomethane. To the resulting mixture was added dropwise a solution of 0.82 g hydrogen chloride in 34 ml ether. The mixture was stirred 4 hours while warming to room temperature. The solution was filtered and concentrated to give the crude product which was purified by flash chromatography on silica gel eluting with 1:3 ethyl acetate:hexane to give the product (0.57 g 59%) as a gum; nmr (deuteriochloroform): δ4.75 (s,2H), 7.99 (m,2H), 8.54(t,1H).

Step B: Preparation of (±)-5-[(2-chloro-1-hydroxy)ethyl]benzofurazan

To a solution of 0.216 g (1.1 mmoles) 5-[(2-chloro-1-oxo)ethyl]-benzofurazan in 2 ml dry tetrahydrofuran cooled in an ice-bath was added dropwise 0.60 ml (0.60 mmole) 1.0M borane/tetrahydrofuran solution. The solution was stirred for 3 hours, quenched with 1 ml of 1:1 tetrahydrofuran:water, 1 ml water, then 2 ml saturated potassium sodium tartrate solution, and extracted with 2×5 ml ethyl acetate. The combined extracts were washed with 2 ml water and brine, dried, and the solvent was removed in vacuo to give 0.205 g crude product. The product was purified by flash chromatography on silica gel eluting with 1:3 ethyl acetate:hexane to give the benzofurazan (0.058 g 26%) as a gum; nmr (deuteriochloroform): δ2.90 (broad S, 1H, —OH), 3.70 (d of d, 1H), 3.85 (d of d, 1H), 5.02 (m, 1H), 7.43 (d of d, 1H), 7.87 (d, 1H), 7.92 (d, 1H).

Step C: Preparation of (±)-1-[2-(benzofurazan-5-yl)-2-hydroxyethyl]-4-[2-(2-pyridyl)ethyl]piperazine A mixture of 0.020 g (0.10 mmole) (±)-5-[(2-chloro-1-hydroxy)ethyl]benzofurazan, 0.017 g (0.20 mmole) sodium bicarbonate, and 0.023 g (0.12 mmole) 1-[2-(2-pyridyl)ethyl]piperazine [(Chem. Phar. Bull., 32, 553 (1984)] in 0.5 ml ethanol was heated at reflux for 4 hours. The solvent was removed in vacuo, the residue was partitioned between 1 ml water and 5 ml ethyl acetate, and the layers were separated. The aqueous layer was extracted with 5 ml ethyl acetate. The combined extracts were washed with 0.5 ml water and brine, dried, and the solvent was removed in vacuo to give 0.027 g (77%) crude product as an oil. The oil was crystallized from 1:10 methylene chloride:ether to give the piperazine (0.016 g, 46%) mp 121°–123° C.

Anal. Calcd for $C_{19}H_{23}N_5O_2 \cdot 0.40\ H_2O$: C, 63.28; H, 6.65; N, 19.42. Found: C, 63.36; H, 6.51; N, 19.48.

EXAMPLE 19

(±)-1-[2-(Benzofurazan-5-yl)-2-hydroxyethyl]-4(4-pyridyl)piperazine

Prepared by the procedure of Example 18 from 0.040 g (0.20 mmole) (±)-5-[(2-chloro-1-hydroxy)ethyl]benzofurazan, 0.034 g (0.40 mmole) sodium bicarbonate and 0.036 g (0.22 mmole) 1-(4-pyridyl)piperazine (*J. Med. Chem.*, 8, 104 (1965)) in 1 ml ethanol to give 0.015 g (237.) product, m.p. 159°–162° C.

Anal Calcd for $C_{17}H_{19}N_5O_2$: C, 62.76; H, 5.89; N, 21.52. Found: C, 63.09; H, 5.92; N, 21.31.

EXAMPLE 20

1-(4-Methanesulfonamidophenyl)-2-{N-[2-benzofurazan-5-oxy)ethyl]-N-methylamino}ethane hydrochloride

Step A: Preparation of 5-(2-bromoethoxy)benzofurazan

Sodium hydroxide (40 mg, 1 mmol) was added to a solution of 5-hydroxybenzofurazan (136 mg, 1 mmol) in ethanol (2 ml) and the mixture was stirred at room temperature for 30 minutes, 1,2-dibromoethane (0.26 ml, 0.56 g, 3 mmol) was added and the mixture was heated under reflux for 20 hours, cooled and the solvent was evaporated under reduced pressure. Aqueous sodium bicarbonate (saturated, 10 ml) was added and the mixture was extracted with dichloromethane (3×10 ml). The combined organic fractions were dried ($Na_2SO_4$) and evaporated under reduced pressure. The residue was purified by flash column chromatography on silica gel, eluting with hexane/10% ethyl acetate to give the benzofurazan as a pale yellow oil (99 mg, 41%).

$\delta H$ ($CDCl_3$) 7.74 (1H, d, J 9.6 Hz), 7.16 (1H, dd, J 9.6, 2.0 Hz), 6.85 (1H, d, J 2.0 Hz), 4.39 (2H, t, J 6.0 Hz), and 3.72 (2H, t, J 6.0 Hz).

Step B: Preparation of 5-(2-methylaminethoxy)benzofurazan hydrobromide

To a solution of 5-(2-bromoethoxy)benzofurazan (0.84 g, 3.4 mmol) in ethanol (45 ml), contained within a Fisher-Porter pressure vessel cooled with ice/acetone was added methylamine (45 ml). The vessel was sealed, the bath removed and the solution was stirred at room temperature overnight. The reaction mixture was concentrated under reduced pressure and the residue flushed with ethanol. Recrystallization from ethyl acetate-hexane gave 5-(2-methylaminoethoxy)benzofurazan hydrobromide (0.75 g, 81%): $^1H$ NMR (DMSO) $\delta 2.68$ (s, 3H), 3.45 (t, 2H), 4.43 (t, 2H), 7.34 (m, 2H), 8.04 (d, 1H, J=9.6 Hz), 8.76 (bs, 2H).

Step C: Preparation of 1-(4-Methanesulfonamidophenyl)-2-{N-[2-(benzofurazan-5-oxy)ethyl]-N-methylamino}ethane hydrochloride A solution of 4-[2-(4-methanesulfonyloxy)ethyl]methanesulfonanilide (100 mg, 0.34 mmol) 5-(2-methylaminoethoxy)benzofurazan hydrobromide (93.2 mg, 0.34 mmol) and diisopropylamine (0.13 ml, 0.75 mmol) in dimethylformamide (1.5 ml) was heated at 80° C. for 2 hours. Solvent evaporation and flash chromatography (silica gel, methanol-chloroform, 3%) gave an oil; salt formation and trituration with ethyl acetate gave 1-(4-methanesulfonamidophenyl)-2-{N-[2-(benzofurazan-5-oxy)ethyl]-N-methylamino}ethane hydrochloride (19 mg, 13%); mp 169°–171° C.

Anal Calcd. for $C_{18}H_{22}N_4O_4S \cdot HCl \cdot \frac{1}{2}\ H_2O$: C, 49.58; H, 5.56; N, 12.85. Found: C, 49.43; H, 5.23; N, 12.66.

EXAMPLE 21

1-(Benzofurazan-5-yl)-2-{N-[2-(benzofurazan-5-oxy)-ethyl]-N-methylamino}ethane hydrochloride A suspension of 5-(2-bromoethyl)benzofurazan (245 mg, 1.08 mmol), 5-(2-methylaminoethoxy)benzofurazan hydrobromide (100 mg, 0.36 mmol), sodium bicarbonate (134 mg, 1.6 mmol) and lithium iodide (2 mg) in ethanol (7.0 ml) was heated at reflux temperature overnight. The reaction mixture was concentrated under reduced pressure and saturated sodium bicarbonate solution added. Extraction with methylene chloride, drying and solvent evaporation gave an oil. Flash chromatography (silica gel, methanol-chloroform, 1%), salt formation and trituration with hexane gave 1-(benzofurazan-5-yl)-2-{N-[2-(benzofurazan-5-oxy)ethyl]-N-methylamino}ethane, hydrochloride (31 mg, 23%); mp 214°–216° C.

Anal Calcd for $C_{17}H_{17}N_5O_3 \cdot HCl$: C, 54.32; H, 4.84; N, 18.64 Found: C, 53.97; H, 4.53; N, 18.51.

EXAMPLE 22

N-(Benzofurazan-5-methyl)-N'N'-diethylethylenediamine dihydrochloride 5-(Methanesulfonyloxymethyl)benzofurazan (130 mg, 0.57 mmol) was dissolved in $CH_2Cl_2$ (2 ml), N,N-diethylethylenediamine (0.13 ml, 105 mg, 0.9 mmol) was added and the mixture was stirred at room temperature for 24 hours. The solvent was evaporated under reduced pressure and the residue was purified by flash column chromatography on silica gel, eluting with $CH_2Cl_2/MeOH/NH_3$ (Aq.); 95:5:1, to give a yellow oil which was dissolved in THF. HCl was bubbled through the solution for 2 minutes and the solid was collected and dried in vacuo to give the dihydrochloride as needles (86 mg, 47%), m.p. 159°–160° C.

Elemental analysis for $C_{13}H_{20}N_4O \cdot 2HCl$ Calculated; C 48.60; H 6.90; N 17.44%. Found: C 48.53; H 6.66; N 17.25%.

EXAMPLE 23

N-[2-[1-[2-(5-Benzofurazanyl)ethyl]-4-piperidinyl]-2,3-dihydro-3-oxo-1H-inden-5-yl]methanesulfonamide

Step A: Preparation of 6-nitro-2-(1-methyl-4-piperidyl)-1-oxo-2-indanecarboxamide To an ice cold solution of 2-(1-methyl-4-piperidyl)-1-oxo-2-indanecarboxamide hydrochloride (5.5 g, 0.0178 mol) in 27 mL of concentrated sulfuric acid was added dropwise over 5 minutes 2.20 g of 90% nitric acid dissolved in 6.8 mL of cold concentrated sulfuric acid. After the addition was complete. the solution was stirred at 0° C. for two hours and then was poured onto ice. The solution was made basic by the addition of solid sodium bicarbonate, and the mixture was extracted with three 100 mL portions of chloroform. The combined chloroform extracts were washed with water, dried over magnesium sulfate, filtered, and the solvent was removed under reduced pressure. The residue was recrystallized from absolute ethanol to give 4.42 g (78% yield)) of 6-nitro-2-(1-methyl-4-piperidyl)-1-oxo-2-indane carboxamide, mp 189°-190° C.

Anal. Cal'd. for $C_{16}H_{19}N_3O_4$: C, 60.55; H, 6.04; N, 13.24. Found: C, 60.72; H, 6.05; N, 13.18.

Step B: Preparation of 6-nitro-2-(1-methyl-4-piperidyl)-indan-1-one

A solution of 4.42 g of 6-nitro-2-(1-methyl-4-piperidyl)-1-oxo-2-indanecarboxamide in 60 mL of 6N hydrochloric acid was stirred and refluxed for one hour. The solution was cooled in an ice bath and made basic by the addition of 20% aqueous sodium hydroxide. The mixture was extracted with three 100 mL portions of ether. The combined extracts were dried over magnesium sulfate, filtered, and the ether was removed under reduced pressure to give 3.72 g (97%) of 6-nitro-2-(1-methyl-4-piperdyl)-indan-1-one as a low melting crystalline solid.

Step C: 6-Methanesulfonamido-2-(4-piperidyl)-indan-1-one hydrochloride

A solution of 1.86 g (0.0068 mol) of 6-nitro-2-(1-methyl-4-piperidyl)indan-1-one in 50 mL of absolute ethanol and 50 mL of tetrahydrofuran was hydrogenated at 10 psi over Raney nickel catalyst. After 2.5 hours, the catalyst was removed by filtration and the solvent was evaporated to give 1.76 g of crystalline 6-amino-2-(1-methyl-4-piperidyl)indan-1-one. To a solution of 1.04 g (0.00426 mol) of the 6-amino compound in 20 mL of methylene chloride and 3.4 g of pyridine was added 0.61 g (0.005 mol) of methanesulfonyl chloride. The mixture was stirred at room temperature for two hours, after which time it was poured onto water and made basic by the addition of a saturated sodium bicarbonate solution. The mixture was concentrated to dryness in vacuo, and the solid residue was extracted with two 50 mL portions of methylene chloride. Evaporation of the methylene chloride gave 1.56 g of 6-methanesulfonamido-2-(1-methyl-4-piperidyl)indane-1-one as a colorless foam.

To a solution of 1.35 g (0.00419 mol) of 6-methanesulfonamido-2-(1-methyl-4-piperidyl)indan-1-one in 46 mL of 1,2-dichloroethane was added 1.35 g (0.0063 mol) of 1,8-bis(dimethylamino)naphthalene. The solution was cooled in an ice bath and 1.80 g (0.0126 mol) of 1-chloroethylchloroformate was added dropwise over 5 minutes. The mixture was allowed to warm to room temperature and then was refluxed for 5 hours. The cooled mixture was filtered through a small column of silica gel using methylene chloride to wash the column. The eluate was evaporated in vacuo. The residual 1.35 g of thick oil was dissolved in 10 mL of methanol, and the solution was refluxed for 24 hours. Evaporation of the methanol and crystallization of the residue. from methanol afforded 6-methanesulfonamido-2-(4-piperidyl)indan-1-one hydrochloride as a hemi methanol solvate salt: mp 254°-256° (dec.).

Anal. Cal'd. for $C_{15}H_{20}N_2O_3S.HCl.0.5CH_3OH$: C, 51.58; H, 6.42; N, 7.76. Found: C, 51.69; H, 6.36; N, 8.00.

Step D:
N-[2-[1-[2-(5-Benzofurazanyl)ethyl]-4-piperidinyl]-2,3-dihydro-3-oxo-1H-inden-5-yl]methanesulfonamide In the manner described in Example 14, 6-methanesulfonamido-2-(4-piperidyl)-indan-1-one hydrochloride (0.20 g, 0.58 mmol), 5-(2-bromoethyl)benzofurazan (0.395 g, 1.74 mmol), sodium bicarbonate (0.146 g, 1.74 mmol) and potassium iodide (20 mg), in 20 mL of acetonitrile were heated under reflux for 30 hours. After purification by flask column chromatography on silica gel eluting with 5% methanol in chloroform saturated with ammonia (gas), and treatment with ethanol HCl, crystallization from methanol gave the title compound as a white solid, mp 214°-217° C.

Anal. Calcd for $C_{23}H_{26}N_4O_4S.HCl.CH_3OH$: C, 55.11; H, 5.97; N, 10.71. Found: C, 54.82; H, 5.80; N, 10.87.

Following the general procedures outlined in the present specification and the specific teachings of these examples, the following compounds were also prepared:

N-[2-[[4-(5-benzofurazanylcarbonyl)-1-piperidinyl]methyl]-6-quinolinyl]methanesulfonamide dihydrochloride having the formula

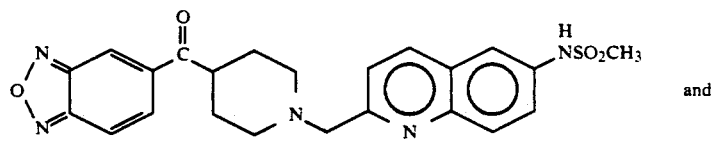

and

N-[2-[1-[2-(5-benzofurazanyl)ethyl]-piperidinyl]-2,3-dihydro-3-oxo-1H-inden-5-yl]methanesulfonamide monohydrochloride having the formula

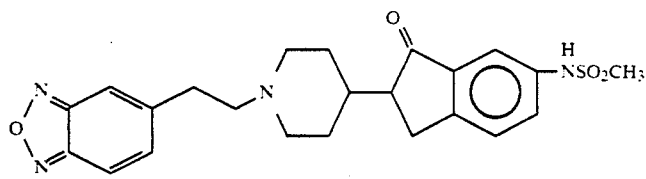

EXAMPLE 24

In Vitro Test for Class III Antiarrhythmic Activity

Purpose

This in vitro assay is designed to assess possible potassium channel blocking activity of a compound based on its ability to prolong effective refractory period (ERP) in isolated papillary muscle.

Tissue Preparation

Ferrets (700 to 1200 grams) are anesthetized with 0.7 ml of a mixture of xylazine and ketamine HCL in 1:7 ratio. Papillary muscles from the right ventricle are quickly excised from the isolated heart and mounted in 50 ml organ batch containing Krebs-Henseleit solution (pH=7.2-7.4) at 37° C. The composition of the solution in millimoles pr liter are as follows: NaCl, 118; KCl, 4.7; $NaHCO_3$, 23; $CaCl_2 \cdot 2H_2O$ 2.0; $MgSO_4 \cdot 7H_2O$, 1.2; $KH_2PO_4$, 1.2; Dextrose, 11.1. Timolol ($10^{-7}M$) is added to the solution to block the effects of catecholamines released during stimulation of the muscles. This solution is aerated with 95% $O_2$ and 5% $CO_2$. The tissue is stimulated at 1 Hz at one msec pulse duration by a square wave stimulator at a voltage 30% above threshold through platinum electrodes that touch the tissue just above the bottom attachment point. The tendenous end of the tissue is connected by thread to an isometric force transducer leading to a polygraph.

Effective Refractory Period (ERP) Measurement

The ERP is determined by a standard 2 pulse protocol. Both pulses are stimulated at 1.3× voltage threshold. Whole pacing the tissue at a basal frequency of 1 Hz, a single extra stimulus is delivered after a variable time delay. The shortest delay resulting in a propagated response is defined as the ERP.

Protocol

1. Tissues are mounted with a resting tension of 0.5 gms, stimulated at 1 Hz, and allowed to equilibrate for 2 hours with washings at 15-20 minute intervals.
2. Voltage is adjusted to 30% above threshold and resting tension is adjusted for maximum developed tension, and the tissue is allowed 5 min. reequilibration time.
3. Effective refractory period is measured at 1 Hz. Changes in resting tension and developed force are noted.
4. After equilibration, ERP's and developed force are measured at 30 minutes following the addition of increasing cumulative concentrations for test agest to the organ bath. Four to five concentrations of test agents were used to generate a concentration-response curve.
5. Four tissues per compound are tested.

Results

Employing the above protocol, it has been found that the effective concentration of most of the compounds of this invention required to increase the refractory period by an increment of 25% above base-line is less than or equal to 10 micromolar, i.e. $EC_{25} \leq 10$ μM, whereas sotalol in the same protocol has an $EC_{25} \sim 20$ micromolar.

EXAMPLE 25

Preparation of intravenous solutions

A solution containing 10 mg of active ingredient per ml of injectable solution is prepared in the following manner.

A mixture of 0.5 mg of active ingredient and is dissolved in 1 ml of acetate buffer. The pH is adjusted using aqueous sodium hydroxide to about pH 5.5.

If it is desired that the intravenous solution be used for multi-dose purposes, 1.0 mg of methyl-p-hydroxy benzoate (methyl paraben) and 0.10 mg of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg, respectively, of active ingredient per ml of solution are similarly prepared substituting the indicated amount for the above-illustrated 10 mg quantity. Bulk injectable solutions of convenient volume for subsequent delivery in unit dosage form are readily prepared following the above procedure.

EXAMPLE 26

Tablet Preparation

Tablets containing 1.0, 2.0, 25.0, 26.0, 50.0 and 100.0 mg, respectively, of active ingredient are prepared as illustrated below.

TABLE FOR DOSES CONTAINING FROM 1-25 MG OF THE ACTIVE COMPOUND

|  | Amount-mg | | |
| --- | --- | --- | --- |
| Active ingredient | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

TABLE FOR DOSES CONTAINING FROM 26-200 MG OF THE ACTIVE COMPOUND

|  | Amount-mg | | |
| --- | --- | --- | --- |
| Active ingredient | 26.0 | 50.0 | 100.0 |
| Microcrystalline cellulose | 25.0 | 100.0 | 200.0 |
| Modified food corn starch | 2.21 | 4.25 | 8.5 |
| Magnesium stearate | .39 | 0.75 | 1.5 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100.0 mg of active ingredient per tablet.

What is claimed is:

1. A compound of structural formula:

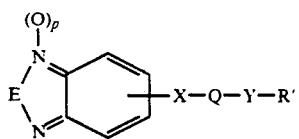

or a pharmaceutically acceptable salt thereof, wherein:
Q is piperazine or piperidine;
X and Y are independently:

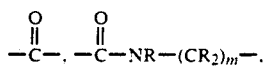

$-(CR_2)_m-$, $-O(CR_2)_m-$, $-(CR_2)_mO-$, $-SO_2-$, $-CH_2NR(CR_2)_m$ or a bond when p is 0, and R is H or $C_{1-6}$alkyl;
m is 1, 2 or 3;
E is $-O-$ or $-S-$
p is 0, or 1;
$R^1$ is hydrogen or a mono- or bicyclic system selected from:

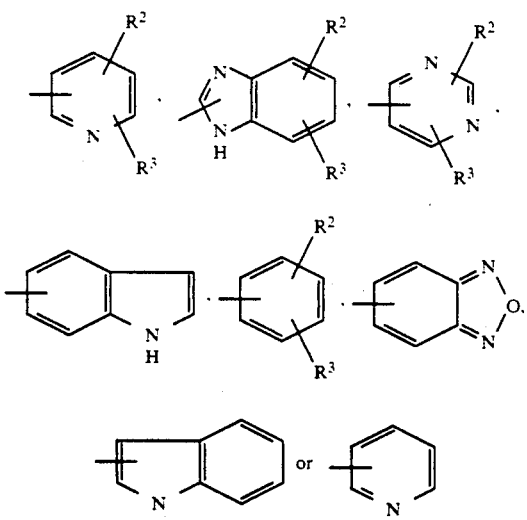

$R^2$ and $R^3$ are independently selected from:
1) hydrogen,
2) $C_{1-3}$ alkyl, either unsubstituted or substituted with
   a) $-N(R)_2$,
   b) $-CON(R)_2$,
   c) $-CO(C_{1-6}$alkyl),
   d) $-O(C_{1-6}$alkyl),
   e) $-OH$, or
   f) $-S(O)_n(C_{1-6}$alkyl) wherein n is 0, 1 or 2;
3) $C_{1-3}$ alkoxy,
4) $-N(R)SO_2C_{1-6}$alkyl, 5) $-N(R)SO_2(CH_2)_nCO_2 C_{1-6}$alkyl.
6) $-NO_2$,
7) $-N(R)COC_{1-3}$alkyl,
8) $-N(R)SO_2-C_6H_4-R$
9) $-NHCO-C_6H_4-R$,
10) $-N(R)_2$,
11) halo,
12) $-C_{2-6}$alkanoyl,
13) $-CON(R)_2$,
14) $-CN$,
15) $-CO_2 C_{1-6}$alkyl
16) benzoyl, either unsubstituted or substituted with $C_{1-6}$alkyl, $C_{1-6}$alkoxy, halo or hydroxy
17) $-NRCOO(C_{1-6}$alkyl),
18) $-NRCOO$ phenyl either unsubstituted or substituted with $C_{1-6}$alkyl, $C_{1-6}$alkoxy, hydroxy or halo,
19) $-NR CON(R)_2$,
20) $-S(O)_nC_{1-6}$alkyl,
21) $-S(O)_n$phenyl, either unsubstituted or substituted with $C_{1-6}$alkyl, $C_{1-6}$alkoxy, hydroxy, or halo,
22) $-CF_3$,
23) $-$phenyl, either unsubstituted or substituted with $C_{1-6}$alkyl, $C_{1-6}$alkoxy, halo, or hydroxy,
24) imidazolyl, or
25) $-SO_2 N(R)_2$, $R^2$ and $R^3$ taken together may be methylenedioxy or ethylenedioxy.

2. The compound of claim 2 wherein $R^1$ is 4-methanesulfonamidophenyl, benzofurazan-5-yl, pyridyl or benzofurazan-N-oxide-5(or 6)-yl.

3. A compound selected from:
4-[N-(benzofurazan-N-oxide-5(or 6)-carbonyl)aminomethyl]-1-[2-(2-pyridyl)ethyl]piperidine;
1-(benzofurazan-N-oxide-5(or 6)-carbonyl)-4-(4-pyridyl)piperazine;
1-(benzofurazan-N-oxide-5(or 6)-carbonyl-4-(4-nitrobenzyl)piperazine;
1-(benzofurazan-N-oxide-5(or 6)-carbonyl-4-(2-pyrimidinyl)piperazine;
1-(benzofurazan-N-oxide-5(or 6)-carbonyl-4-[2-(2-pyridyl)ethyl]piperazine;
1-(benzofurazan-5-carbonyl)-4-(4-pyridyl)piperazine;
1-(benzofurazan-5-carbonyl)-4-[2-(2-pyridyl)ethyl]piperazine;
4-[N-(benzofurazan-5-carbonyl)-aminomethyl]-1-[2-(2-pyridyl)ethyl]piperidine;
1-(benzofurazan-5-carbonyl)-4-(4-nitrobenzyl)piperazine;
1-(benzofurazan-5-carbonyl)-4-(2-pyrimidinyl)piperazine;
1-(benzofurazan-5-carbonyl)-4-[1-(4-nitrophenyl)ethyl]piperazine;
1-(benzofurazan-5-carbonyl)-4-(2-phenylethyl) piperazine;
1-benzofurazan-5-carbonyl)-4-[2-(benzofurazan-5-yl)ethyl]piperazine;
1-benzofurazan-5-carbonyl)-4-[2-(4-methanesulfonamidophenyl)ethyl]piperazine;
4-(benzofurazan-5-methyl-1-(4-pyridyl)piperazine;
1-(benzofurazan-5-methyl)-4-[2-(2-pyridyl)ethyl]piperazine;
1-(benzofurazan-5-methyl)-4-[2-(4-nitrophenyl)-ethyl]piperazine;
1-(benzofurazan-5-methyl)-4-[2-(4-methanesulfonamidophenyl)ethyl]piperazine;

4-[2-(benzofurazan-5-yl)ethyl]-1-benzofurazan-5-methyl)piperazine;

1-[2-(6-methyl-2-piperidyl)ethyl]-4-(benzofurazan-5-carbonyl)piperidine;

1-[2-(benzofurazan-5-yl)ethyl]-4-(benzofurazan-5-carbonyl)piperidine;

1-[2-(4-methanesulfonamidophenyl)ethyl]-4-(benzofurazan-5-carbonyl)piperidine;

1-[2-(4-nitrophenyl)ethyl]-4-(benzofurazan-5-carbonyl)piperidine;

4-[2-benzofurazan-5-yl)ethyl]-1-(indole-5-carbonyl)piperazine;

1-[2-(benzofurazan-5-yl)-2-hydroxyethyl]-4-[2-(2-pyridyl)ethyl]piperazine;

1-[2-(benzofurazan-5-yl)-2-hydroxyethyl]-4-(4-pyridyl)piperazine;

N-[2-[[4-(5-benzofurazanylcarbonyl)-1-piperidinyl]methyl]-6-quinolinyl]methanesulfonamide;

N-[2-[1-[2-(5-benzofurazanyl)ethyl]-4-piperidinyl]-2,3-dihydro-3-oxo-1H-inden-5-yl]methanesulfonamide.

4. A pharmaceutical formulation comprising a carrier and an effective antiarrhythmic amount of a compound of claim 1.

5. The pharmaceutical formulation of claim 4 comprising, in addition, a pharmaceutically effective amount of a Class I, II or IV antiarrhythmic agent.

6. A method for the prevention or treatment of arrhythmia in a member of a mammalian species in need of such treatment which comprises the administration of an effective antiarrhythmic amount of a compound of claim 1.

* * * * *